(12) United States Patent
Aoki

(10) Patent No.: US 12,257,020 B2
(45) Date of Patent: Mar. 25, 2025

(54) VITAL INFORMATION DISPLAYING DEVICE, DISPLAY CONTROLLING DEVICE, AND NON-TRANSITORY COMPUTER-READABLE MEDIUM

(71) Applicant: NIHON KOHDEN CORPORATION, Tokyo (JP)

(72) Inventor: Toshiki Aoki, Tokorozawa (JP)

(73) Assignee: NIHON KOHDEN CORPORATION, Tokyo (JP)

(\*) Notice: Subject to any disclaimer, the term of this patent is extended or adjusted under 35 U.S.C. 154(b) by 1158 days.

(21) Appl. No.: 16/976,374

(22) PCT Filed: Feb. 15, 2019

(86) PCT No.: PCT/JP2019/005644
§ 371 (c)(1),
(2) Date: Aug. 27, 2020

(87) PCT Pub. No.: WO2019/167680
PCT Pub. Date: Sep. 6, 2019

(65) Prior Publication Data
US 2021/0369112 A1    Dec. 2, 2021

(30) Foreign Application Priority Data
Mar. 1, 2018  (JP) ................. 2018-036671
Dec. 27, 2018  (JP) ................. 2018-244985

(51) Int. Cl.
*A61B 5/00* (2006.01)
*A61B 5/083* (2006.01)

(52) U.S. Cl.
CPC ............ *A61B 5/0004* (2013.01); *A61B 5/083* (2013.01); *A61B 5/7235* (2013.01); *A61B 5/742* (2013.01)

(58) Field of Classification Search
CPC ..... A61B 5/0004; A61B 5/083; A61B 5/7235; A61B 5/742
(Continued)

(56) References Cited

U.S. PATENT DOCUMENTS

| | | | |
|---|---|---|---|
| 2009/0054743 A1* | 2/2009 | Stewart | G06T 11/206 |
| | | | 600/301 |
| 2010/0113898 A1 | 5/2010 | Kim et al. | |

(Continued)

FOREIGN PATENT DOCUMENTS

| | | |
|---|---|---|
| JP | 2017-035473 A | 2/2017 |
| KR | 2010-0048324 A | 5/2010 |

OTHER PUBLICATIONS

International Search Report issued in Patent Application No. PCT/JP2019/005644 dated May 23, 2019.
(Continued)

*Primary Examiner* — Aaron F Roane
(74) *Attorney, Agent, or Firm* — MCDONALD HOPKINS LLC

(57) ABSTRACT

An input interface is configured to receive a signal corresponding to vital information that exhibits temporal variation. When at least one instruction stored in a memory is executed by a processor, waveform information (W) is generated based on the signal; a value of a profile factor of the waveform information (W) is obtained every time a predetermined time period is elapsed; and the value is displayed on the display section (15). The profile factor includes at least one of a rising angle, a top portion angle, a falling angle, a rising velocity, an absolute value of the rising velocity, a top portion velocity, an absolute value of the top portion velocity, a falling velocity, an absolute angle of the falling velocity, an under-waveform area, a rising-falling
(Continued)

time interval, a falling-rising time interval, a rising-rising time interval and a falling-falling time interval.

6 Claims, 11 Drawing Sheets

(58) Field of Classification Search
USPC .......................................................... 600/301
See application file for complete search history.

(56) References Cited

U.S. PATENT DOCUMENTS

| | | |
|---|---|---|
| 2015/0157241 A1 | 6/2015 | Yamamori et al. |
| 2016/0196635 A1 | 7/2016 | Cho et al. |
| 2016/0287170 A1 | 10/2016 | Ronen et al. |
| 2017/0035325 A1 | 2/2017 | Aoki et al. |

OTHER PUBLICATIONS

Written Opinion issued in Patent Application No. PCT/JP2019/005644 dated May 23, 2019.
Japanese Office Action issued in Japanese Patent Application No. 2018-244985.

* cited by examiner

FIG. 5A
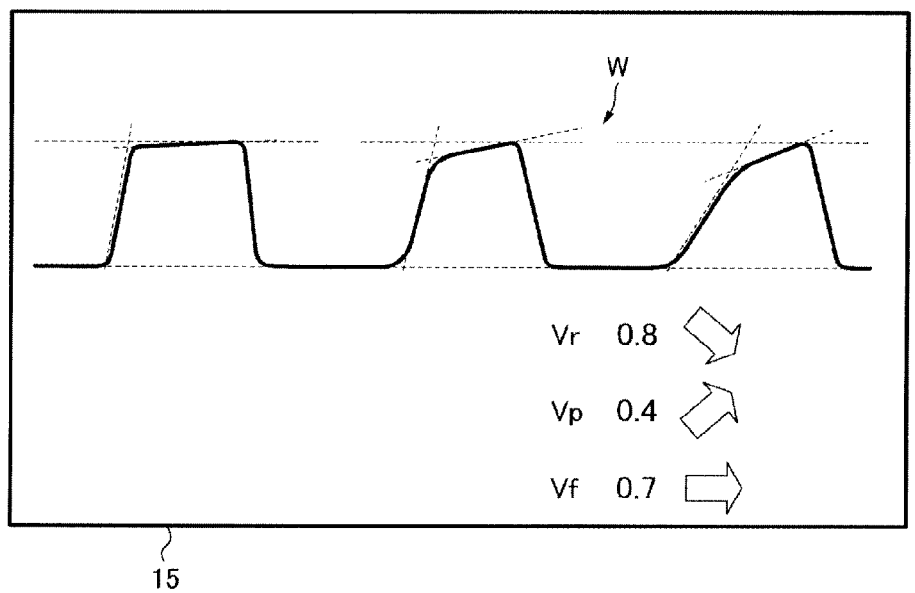
FIG. 5B
| Vr | 1.9 | Vr | 1.3 | Vr | 0.8 |
| Vp | 0.1 | Vp | 0.2 | Vp | 0.4 |
| Vf | 0.7 | Vf | 0.7 | Vf | 0.7 |
FIG. 5C
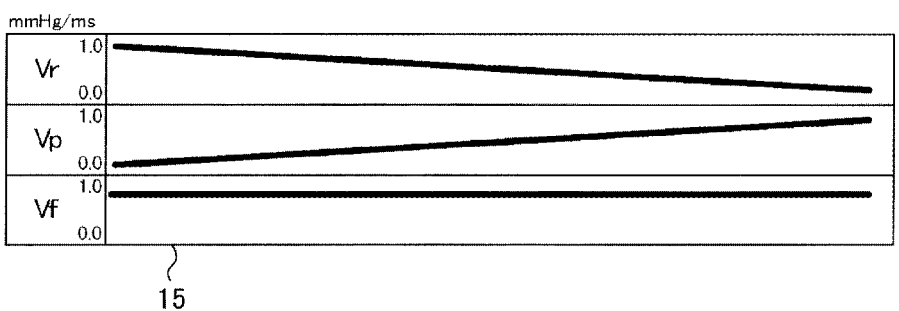

VITAL INFORMATION DISPLAYING DEVICE, DISPLAY CONTROLLING DEVICE, AND NON-TRANSITORY COMPUTER-READABLE MEDIUM

TECHNICAL FIELD

The presently disclosed subject matter relates to a device for displaying vital information of a subject that exhibits temporal variation. The presently disclosed subject matter also relates to a device for controlling display of the vital information, as well as a non-transitory computer-readable medium having stored a computer program for causing the device to perform the display control.

BACKGROUND ART

As the vital information of the subject that exhibits temporal variation, a carbon dioxide concentration (partial pressure) in respiration gas, a pulse wave, an electrocardiogram, an electroencephalogram, or the like may be exemplified. Japanese Patent Publication No. 2017-035473A discloses a device for displaying the temporal variation of carbon dioxide concentration in the respiration gas of a subject in the real time manner. The device includes a display area having a vertical axis and a horizontal axis. The vertical axis represents the carbon dioxide concentration value. The horizontal axis represents the elapse of time. As a result, a waveform indicating the temporal variation of the carbon dioxide concentration value is displayed in the display area.

The vital information as described above has a feature that same or similar variation tendency repeatedly appears. For example, in the case of carbon dioxide concentration, the value increases with the expiration of the subject, and decreases with the inspiration. The condition change or abnormality of the subject appears as a remarkable variation of the waveform profile. The medical worker judges the condition change or abnormality of the subject by noting such a variation.

SUMMARY OF INVENTION

The presently disclosed subject matter is intended to assist judgment of a medical worker based on vital information of a subject that exhibits temporal variation on a display section.

An illustrative aspect of the presently disclosed subject matter provides a vital information displaying device comprising:
 an input interface configured to receive a signal corresponding to vital information that exhibits temporal variation;
 a processor;
 a memory configured to store at least one instruction that is executable by the processor; and
 a display section,
 wherein when the at least one instruction is executed by the processor,
 waveform information is generated based on the signal;
 a value of a profile factor of the waveform information is obtained every time a predetermined time period is elapsed; and
 at least one of the value of the profile factor as obtained, a chronological change of the value, and an indicator indicating the chronological change is displayed on the display section; and
 wherein the profile factor includes at least one of a rising angle, a top portion angle, a falling angle, a rising velocity, an absolute value of the rising velocity, a top portion velocity, an absolute value of the top portion velocity, a falling velocity, an absolute angle of the falling velocity, an under-waveform area, a rising-falling time interval, a falling-rising time interval, a rising-rising time interval and a falling-falling time interval.

An illustrative aspect of the presently disclosed subject matter provides a display controlling device comprising:
 an input interface configured to receive a signal corresponding to vital information that exhibits temporal variation;
 a processor;
 a memory configured to store at least one instruction that is executable by the processor; and
 an output interface,
 wherein when the at least one instruction is executed by the processor,
 waveform information is generated based on the signal;
 a value of a profile factor of the waveform information is obtained every time a predetermined time period is elapsed; and
 a control signal is output from the output interface to cause a display device to display at least one of the value of the profile factor as obtained, a chronological change of the value, and an indicator indicating the chronological change; and
 wherein the profile factor includes at least one of a rising angle, a top portion angle, a falling angle, a rising velocity, an absolute value of the rising velocity, a top portion velocity, an absolute value of the top portion velocity, a falling velocity, an absolute angle of the falling velocity, an under-waveform area, a rising-falling time interval, a falling-rising time interval, a rising-rising time interval and a falling-falling time interval.

An illustrative aspect of the presently disclosed subject matter provides a non-transitory computer-readable medium having stored a computer program including at least one instruction to be executed by a processor of a display controlling device,
 wherein when the at least one instruction is executed by the processor,
 waveform information is generated based on the signal;
 a value of a profile factor of the waveform information is obtained every time a predetermined time period is elapsed; and
 a control signal is output from the output interface to cause a display device to display at least one of the value of the profile factor as obtained, a chronological change of the value, and an indicator indicating the chronological change; and
 wherein the profile factor includes at least one of a rising angle, a top portion angle, a falling angle, a rising velocity, an absolute value of the rising velocity, a top portion velocity, an absolute value of the top portion velocity, a falling velocity, an absolute angle of the falling velocity, an under-waveform area, a rising-falling time interval, a falling-rising time interval, a rising-rising time interval and a falling-falling time interval.

For example, in a case where information corresponding to the rising angle and the top portion angle is displayed for the waveform information related to the carbon dioxide concentration or partial pressure in the respiration gas of the subject, medical workers may be assisted in determining the chronic obstructive pulmonary disease by referring to the displayed information.

For example, in a case where information corresponding to the top portion angle and the falling angle is displayed for the waveform information related to the carbon dioxide concentration or partial pressure in the respiration gas of the subject, medical workers may be assisted in determining the change in the ventilation state of the subject or the respiratory circuit abnormality in the respirator by referring to the displayed information.

For example, in a case where information corresponding to the rising velocity, the top portion velocity and the falling velocity is displayed for the waveform information related to the carbon dioxide concentration or partial pressure in the respiration gas of the subject, medical workers may be assisted in determining the chronic obstructive pulmonary disease by referring to the displayed information.

For example, in a case where information corresponding to the rising angle and the falling angle is displayed for the waveform information related to the carbon dioxide concentration or partial pressure in the respiration gas of the subject, medical workers may be assisted in setting the proper ventilation rate in the respirator by referring to the displayed information.

For example, in a case where information corresponding to the under-waveform area is displayed for the waveform information related to the carbon dioxide concentration or partial pressure in the respiration gas of the subject, medical workers may be assisted in determining the change in the ventilation state of the subject or the respiratory circuit abnormality in the respirator by referring to the displayed information. Alternatively, the medical worker may be assisted in determining the subject's spontaneous respiration or improved ventilation by referencing the displayed information.

For example, in a case where information corresponding to the rising-falling time interval and the falling-rising time interval is displayed for the waveform information related to the carbon dioxide concentration or partial pressure in the respiration gas of the subject, medical workers may be assisted in recognizing the actual I:E rate (the ratio of the inspiratory duration to the expiratory duration) by referring to the displayed information. By comparing the actual I:E ratio with the I:E ratio preset in the respirator, the determination of the ventilation state of the subject may be assisted.

For example, in a case where information corresponding to the rising-rising time interval or the falling-falling time interval is displayed for the waveform information related to the carbon dioxide concentration or partial pressure in the respiration gas of the subject, medical workers may be assisted in determining respiratory depression that has occurred in the subject by referring to the displayed information.

BRIEF DESCRIPTION OF DRAWINGS

FIG. 5A illustrates a third operation example of a display section in the vital information displaying device.

FIG. 5B illustrates the third operation example of the display section in the vital information displaying device.

FIG. 5C illustrates the third operation example of the display section in the vital information displaying device.

DESCRIPTION OF EMBODIMENTS

Examples of embodiments are described in detail below with reference to the accompanying drawings. In each drawing, the scale is appropriately changed in order to make each element to be described have a recognizable size.

Figure 1:
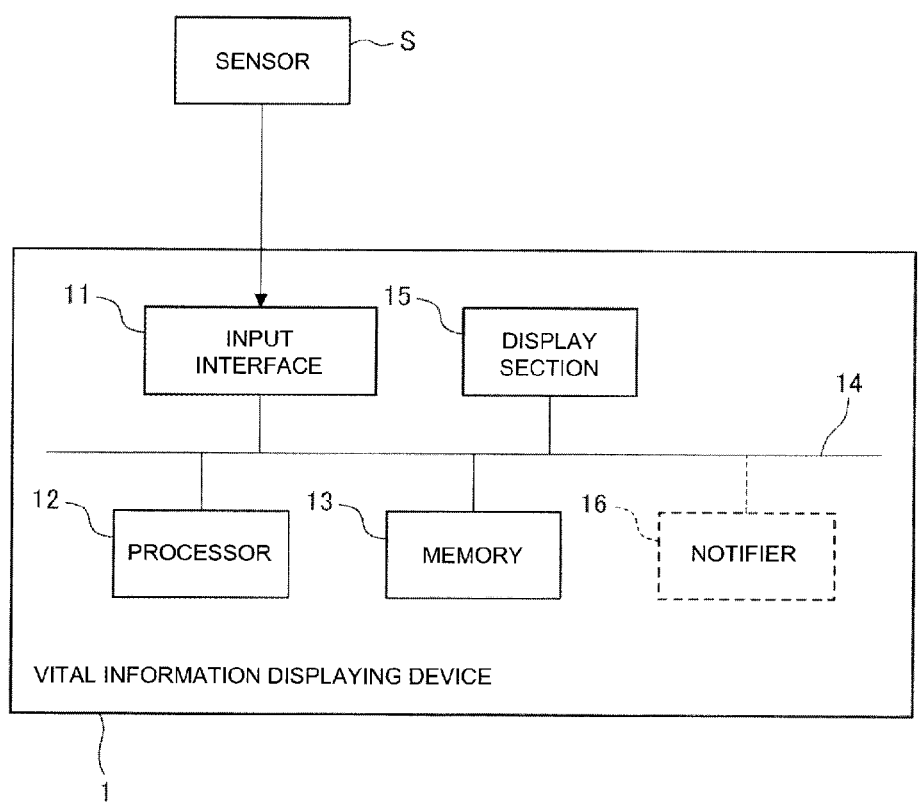
FIG. 1 illustrates a configuration of a vital information displaying device according to an embodiment.

As illustrated in FIG. 1, a vital information displaying device 1 according to an embodiment includes an input interface 11. A signal corresponding to the vital information of the subject detected through a sensor S is input to the input interface 11. Signal input may be via a wired connection or via wireless communication. The input interface 11 includes a circuit for converting an input signal into data necessary for subsequent processing. As the circuit, an A/D conversion circuit, a filter circuit, or the like may be exemplified.

The vital information displaying device 1 includes a processor 12 and a memory 13. As the processor 12, a CPU, an MPU, a GPU, or the like may be exemplified. The processor 12 may include a plurality of processor cores. As the memory 13, a ROM, a RAM, or the like may be exemplified. The memory 13 may store a computer program for executing processing to be described later. The computer program may be stored in the memory 13 in advance, or may be downloaded from an external server via a communication network (not illustrated) and the input interface 11. The computer program may include an artificial intelligence program. As the artificial intelligence program, a neural network trained by deep learning may be exemplified. The computer program is an example of instructions executable by the processor 12. For example, the processor 12 may designate at least a part of the computer program stored in the ROM and load the program on the RAM in order to execute processing described later in cooperation with the RAM.

The processor 12 and the memory 13 are connected to the input interface 11 via a communication bus 14. At least one of the processor 12 and the memory 13 may be provided in a housing independent of the housing in which the input interface 11 is provided, as long as communication with the input interface 11 is possible via a suitable communication interface.

The vital information displaying device 1 includes a display section 15. The display section 15 is connected to the input interface 11, the processor 12, and the memory 13 via the communication bus 14.

In this example, the sensor S detects the carbon dioxide concentration (partial pressure) in the respiration gas of the subject. That is, the sensor S outputs a signal corresponding to the value of the detected carbon dioxide concentration. When the program stored in the memory 13 is executed by the processor 12, waveform information indicating the temporal variation of the carbon dioxide concentration value is generated based on the signal input from the sensor S to the input interface 11.

Figure 2A:
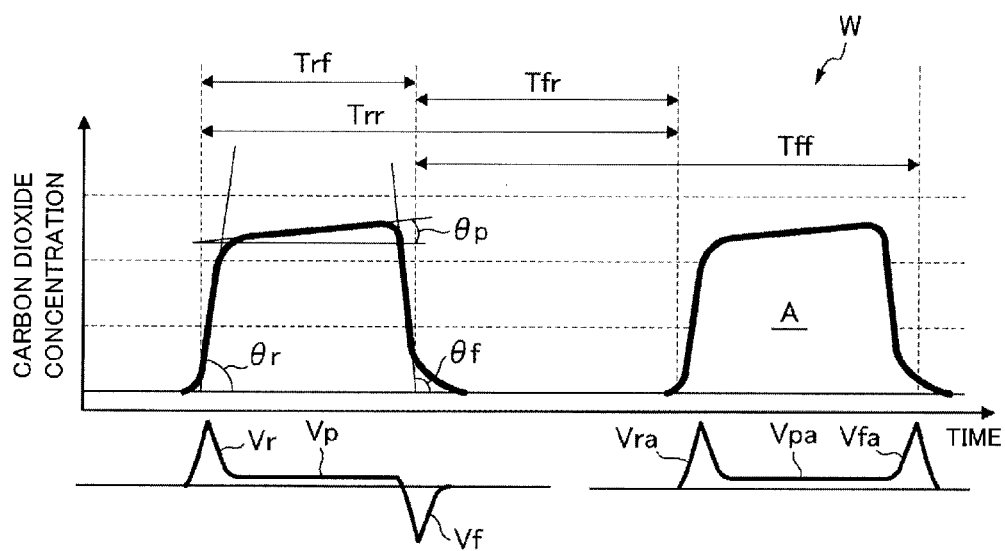
FIG. 2A illustrates profile factors of waveform information to be displayed on the vital information displaying device.

FIG. 2A illustrates an example of the waveform information W to be generated. The vertical axis represents the value of the carbon dioxide concentration. The horizontal axis represents the elapse of time. Exhalation of the subject increases the carbon dioxide concentration value, whereas inhalation of the subject decreases the carbon dioxide concentration value. Due to repeated respirations of the subject, increasing and decreasing of the carbon dioxide concentration value are repeated alternately.

Subsequently, a value of a profile factor of the waveform information W is obtained every predetermined time period T. The "profile factor" is a variety of parameters that characterize the shape of the increasing-decreasing pattern of the carbon dioxide concentration value. Details of each profile factor illustrated in FIG. 2A are as follows.

$\theta_r$: rising angle (gradient of a portion where the concentration value steeply increases)

$\theta_p$: top portion angle (gradient of the portion where the concentration value gently increases near the peak value)

$\theta_f$: falling angle (gradient of a portion where the concentration value steeply decreases)

$V_r$: rising velocity (rate of change at the portion where the concentration value steeply increases)

$V_p$: top portion velocity (rate of change at the portion where the concentration value gently increases near the peak value)

$V_f$: falling velocity (rate of change at the portion where the concentration value steeply decreases)

$V_{ra}$: absolute value of $V_r$ $V_{pa}$: absolute value of $V_p$ $V_{fa}$: absolute value of $V_f$ $T_{rf}$: rising-falling time interval (time interval from the start of increasing to the end of decreasing in the concentration value)

$T_{fr}$: falling-rising time interval (the time interval from the end of the decreasing in the concentration value of one increasing-decreasing pattern to the start of the increasing in the concentration value of the next increasing-decreasing pattern)

$T_{rr}$: rising-rising time interval (time interval from the start of increasing in concentration value of one increasing-decreasing pattern to the start of increasing in concentration value of the next increasing-decreasing pattern)

$T_{ff}$: falling-falling time interval (the time interval from the end of the decreasing in the concentration value of one increasing-decreasing pattern to the end of the decreasing in the concentration value of the next increasing-decreasing pattern)

A: under-waveform area (area of the area surrounded by a baseline indicating a reference concentration value and the waveform)

The "portion where the concentration value steeply increases" can be defined as, for example, a portion where the concentration value increases from 10% to 90% of the peak value. The "portion where the concentration value gently increases" can be defined as, for example, a portion where the concentration value increases from 90% of the peak value to the peak value. The "portion where the concentration value steeply decreases" can be defined as a portion where the concentration value decreases from 90% to 10% of the peak value, for example. The "start of increasing in the concentration value" may be defined, for example, as the time point at which the increasing concentration value reaches 10% of the peak value. The "end of decreasing of the concentration value" can be defined as, for example, a time point when the decreasing concentration value reaches 10% of the peak value.

Alternatively, by obtaining the differential value (variation speed) of the variation in the concentration value, the "portion where the concentration value steeply increases", the "portion where the concentration value gently increases", and the "portion where the concentration value steeply decreases" may be defined. For example, a time period during which the obtained differential value is greater than a predetermined positive threshold value may be defined as a "portion where the concentration value steeply increases". Similarly, a time period during which the differential value is no greater than the predetermined positive threshold value may be defined as a "portion where the concentration value gently increases", and a time period during which the differential value is less than a predetermined negative threshold value may be defined as a "portion where the concentration value steeply decreases".

Figure 2B:
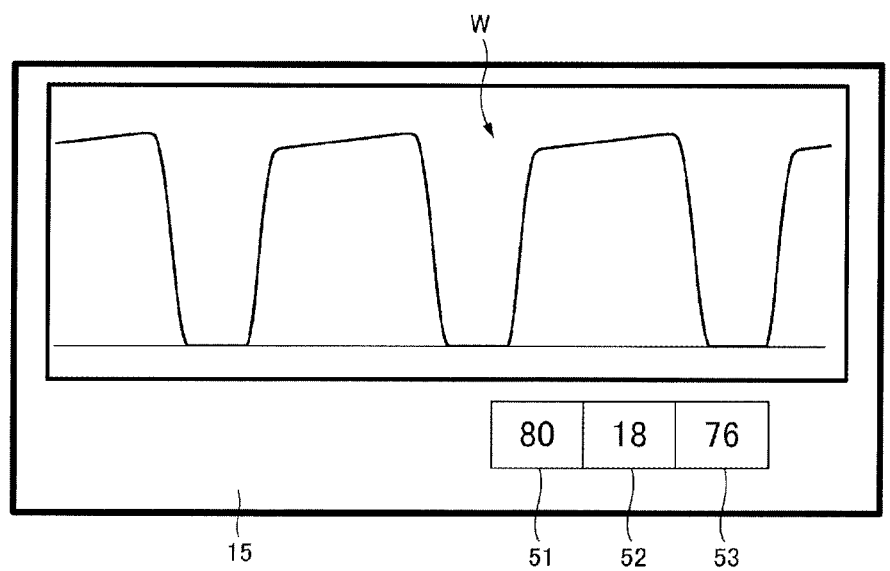
FIG. 2B illustrates values of the profile factors to be displayed on the vital information displaying device.

As shown in FIG. 2B, the waveform information W generated at any time based on the signal input from the sensor S to the input interface 11 is displayed on the display section 15. In addition, the profile factor obtained as described above is displayed on the display section 15 as a value.

In the illustrated example, the display section 15 includes a first display region 51, a second display region 52, and a third display region 53. A numerical value of the rising angle $\theta_r$ is displayed in the first display region 51. A numerical value of the top portion angle $\theta_p$ is displayed in the second display area 52. A numerical value of the falling angle $\theta_f$ is displayed in the third display region 53. These numerical values may be obtained for the latest increasing-decreasing pattern in the waveform information W.

The at least one profile factor to be obtained may be appropriately selected from the group of profile factors described above. Alternatively, after all the profile factors have been obtained, at least one profile factor to be displayed on the display section 15 can be appropriately selected.

The predetermined time period T may be appropriately set in accordance with the obtained profile factor. For example, when at least one of the absolute values of the rising angle [theta]r, the top portion angle [theta]p, the falling angle [theta]f, the rising velocity Vr, the top portion velocity Vp, the absolute value of each of the falling velocities Vf, Vr, Vp, and Vf, the rising-falling time interval Trf, and the under-waveform area A is obtained, the predetermined time period T may be set as a time period in which a single increasing-decreasing pattern of the carbon dioxide concentration value can be contained. When at least one of the falling-rising time interval Tfr, the rising-rising time interval Trr, and the falling-falling time interval Tff is obtained, it can be set as a time period in which the time interval can be contained.

Various information can be read from the variation in the value of the profile factor displayed on the display section 15. Eight specific examples will be described with reference to FIGS. 3A to 10B.

Figure 3A:
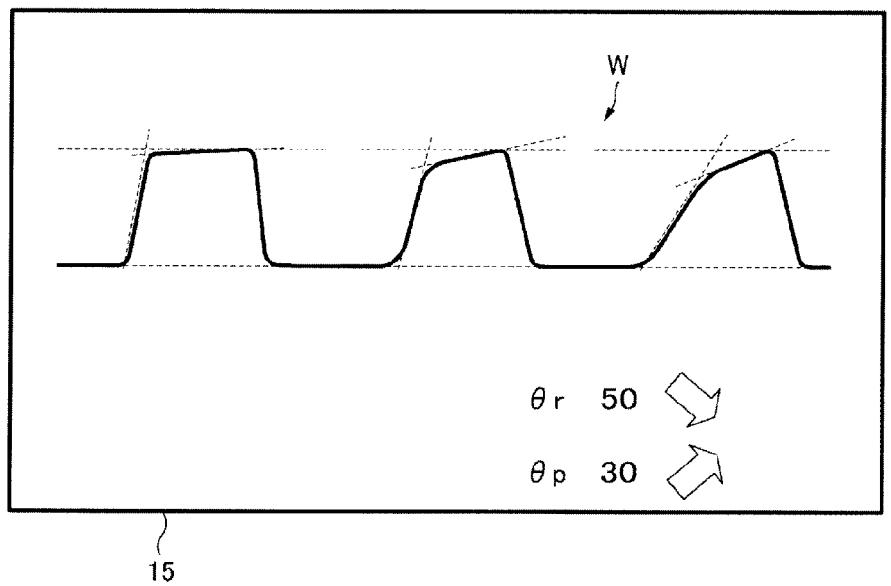
FIG. 3A illustrates a first operation example of a display section in the vital information displaying device.

FIG. 3A shows a first example in which the rising angle [theta]r and the top portion angle [theta]p are obtained as the profile factors. In this example, these profile factors are used to determine chronic obstructive pulmonary disease.

One of the symptoms of the obstructive pulmonary disease is airway stenosis. With the conventional device that obtains a maximum value of the carbon dioxide concentration and a respiration rate per unit time, it is difficult to clearly recognize the progress of the airway stenosis from displayed values thus obtained. The inventor of the present application noticed that characteristic changes appear in the rising angle [theta]r and the top portion angle [theta]p in the increasing-decreasing pattern of the carbon dioxide concentration value as the airway stenosis progresses, and conceived that the determination of the chronic obstructive pulmonary disease can be assisted by displaying information corresponding to these profile factors.

In FIG. 3A, the waveform information W that changes with the progress of the bronchial obstruction is displayed on the display section 15 (the dashed lines are illustrated as a reference and not actually displayed on the display section 15). It can be seen that as the bronchial obstruction progresses, the rising angle [theta]r decreases and the top portion angle [theta]p increases.

Values of the rising angle [theta]r and the top portion angle [theta]p may be displayed on the display section 15. In this case, the value of the most recently obtained profile factor (the value obtained for the rightmost increasing-decreasing pattern) is displayed. Thus, by referring to these values, medical workers may be assisted in determining chronic obstructive pulmonary disease.

Additionally or alternatively, an indicator indicating the chronological change of each value may be displayed on the display 15. In this example, an arrow indicating the increase or decrease of the value of the most recently obtained profile factor (the value obtained for the rightmost increasing-decreasing pattern) with respect to the value of the previously obtained profile factor (the value obtained for the center increasing-decreasing pattern) is displayed as an example of the indicator. In addition to or instead of the arrow, the color of at least one of the text indicating the type of the profile factor and the text indicating the value of the profile factor may be changed in accordance with the increase or decrease. That is, the displayed "color" is also an example of the indicator.

According to such a configuration, the trend of each of the chronological changes of the rising angle [theta]r and the top portion angle [theta]p can be visually recognized more intuitively. Therefore, it is possible to enhance the assistability for the determination of the chronic obstructive pulmonary disease.

Figure 3B:
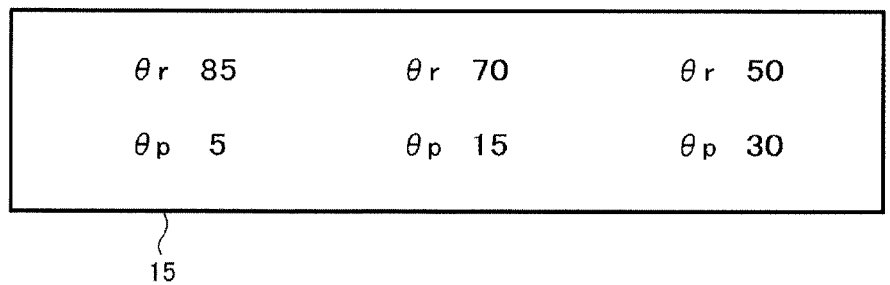
FIG. 3B illustrates the first operation example of the display section in the vital information displaying device.

As shown in FIG. 3B, each time the value of the profile factor is obtained, that is, the value of the profile factor may be displayed in association with each of a plurality of increasing-decreasing patterns displayed on the display section 15. According to such a configuration, it is possible to easily grasp a longer-term trend of each of the chronological changes of the rising angle [theta]r and the top portion angle [theta]p. Therefore, it is possible to enhance the assistability for the determination of the chronic obstructive pulmonary disease.

Figure 3C:
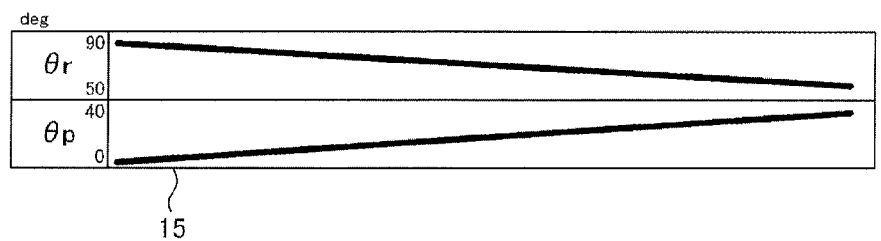
FIG. 3C illustrates the first operation example of the display section in the vital information displaying device.

Additionally or alternatively, as shown in FIG. 3C, each of the chronological changes of the rising angle [theta]r and the top portion angle [theta]p in the time slot displayed on the display section 15 may be displayed in a graph form. With such a configuration, it is also possible to easily grasp a longer-term trend of each of the chronological changes of the rising angle [theta]r and the top portion angle [theta]p. Therefore, it is possible to enhance the assistability for the determination of the chronic obstructive pulmonary disease.

Figure 4A:
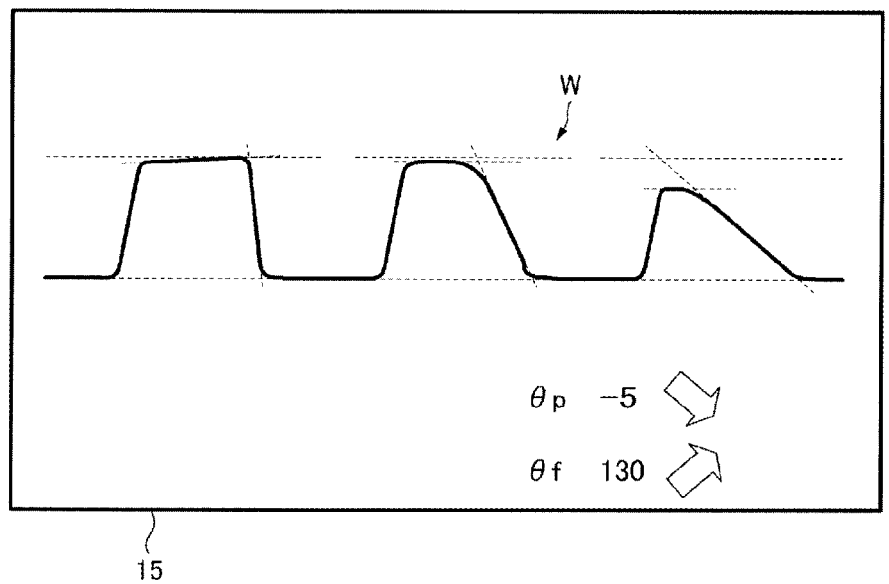
FIG. 4A illustrates a second operation example of a display section in the vital information displaying device.

FIG. 4A shows a second example in which the top portion angle [theta]p and the falling angle [theta]f are obtained as the profile factors. In this example, these profile factors are used to determine a change in the ventilation state of the subject or a respiratory circuit abnormality in a respirator.

When a respirator is used for neonates, exhaled respiration gas may leak to the outside without returning to the respirator because an intubation tube without a cuff is typically used. With the conventional device that obtains a maximum value of the carbon dioxide concentration and a respiration rate per unit time, it is difficult to judge whether the cause of the decrease in the value of the carbon dioxide concentration is due to an increase in the leakage in the respiration circuit or a decrease in the ventilation rate of the subject. The leak rate increases with both increased leakage and decreased ventilation. The inventor of the present application noticed that characteristic changes appear in the top portion angle [theta]p and the falling angle [theta]f in the increasing-decreasing pattern of the carbon dioxide concentration value as the leak rate in the respiratory circuit increases, and conceived that by displaying information corresponding to these profile factors, it is possible to assist the determination of the change in the ventilation state of the subject and the respiratory circuit abnormality.

In FIG. 4A, the waveform information W that changes with an increase in the leak rate or a decrease in the ventilation rate is displayed on the display section 15 (the dashed lines are illustrated as a reference and not actually displayed on the display section 15). It can be seen that as the leak rate increases, the top portion angle [theta]p decreases and the falling angle [theta]f increases.

Values of the top portion angle [theta]p and the falling angle [theta]f may be displayed on the display section 15. In this case, the value of the most recently obtained profile factor (the value obtained for the rightmost increasing-decreasing pattern) is displayed. Thus, by referring to these values, medical workers may be assisted in determining the change in the ventilation state of the subject and the respiratory circuit abnormality in the respirator.

Additionally or alternatively, an indicator indicating the chronological change of each value may be displayed on the display 15. In this example, an arrow indicating the increase or decrease of the value of the most recently obtained profile factor (the value obtained for the rightmost increasing-decreasing pattern) with respect to the value of the previously obtained profile factor (the value obtained for the center increasing-decreasing pattern) is displayed as an example of the indicator. In addition to or instead of the arrow, the color of at least one of the text indicating the type of the profile factor and the text indicating the value of the profile factor may be changed in accordance with the increase or decrease.

According to such a configuration, the trend of each of the chronological changes of the top portion angle [theta]p and the falling angle [theta]f can be visually recognized more intuitively. Therefore, it is possible to enhance the assistability for the determination of the change in the ventilation state of the subject and the respiratory circuit abnormality in the respirator.

Figure 4B:
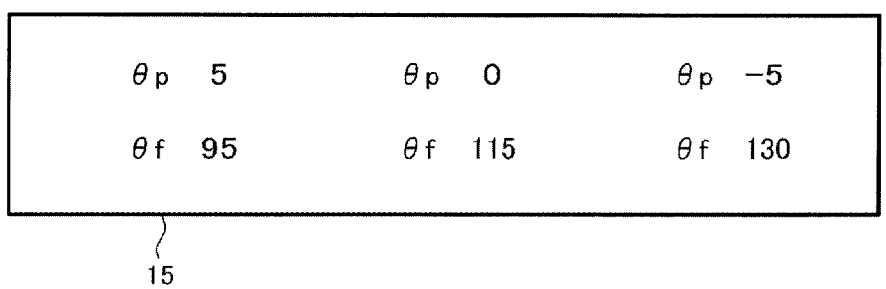
FIG. 4B illustrates the second operation example of the display section in the vital information displaying device.

As shown in FIG. 4B, each time the value of the profile factor is obtained, that is, the value of the profile factor may be displayed in association with each of a plurality of increasing-decreasing patterns displayed on the display section 15. According to such a configuration, it is possible to easily grasp a longer-term trend of each of the chronological changes of the top portion angle [theta]p and the falling angle [theta]f. Therefore, it is possible to enhance the assistability for the determination of the change in the ventilation state of the subject and the respiratory circuit abnormality in the respirator.

Figure 4C:
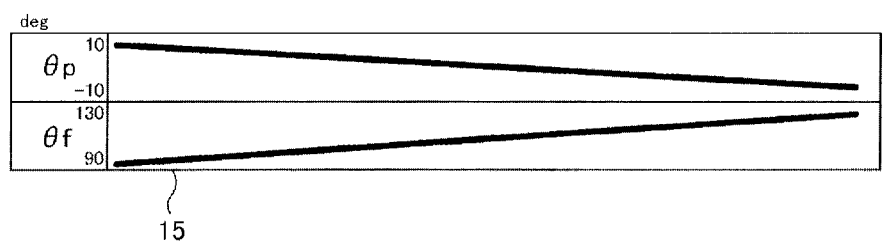
FIG. 4C illustrates the second operation example of the display section in the vital information displaying device.

Additionally or alternatively, as shown in FIG. 4C, the each of chronological changes of the top portion angle [theta]p and the falling angle [theta]f in the time slot displayed on the display section 15 may be displayed in a graph form. With such a configuration, it is also possible to easily grasp a longer-term trend of each of the chronological changes of the top portion angle [theta]p and the falling angle [theta]f. Therefore, it is possible to enhance the assistability for the determination of the change in the ventilation state of the subject and the respiratory circuit abnormality in the respirator.

FIG. 5A shows a third example in which the rising velocity Vr, the top portion velocity Vp, and the falling velocity Vf (or their absolute values) are obtained as the profile factors. In this example, these profile factors are used to determine chronic obstructive pulmonary disease.

One of the symptoms of the obstructive pulmonary disease is airway stenosis. With the conventional device that obtains a maximum value of the carbon dioxide concentration and a respiration rate per unit time, it is difficult to clearly recognize the progress of the airway stenosis from displayed values thus obtained. The inventor of the present application noticed that characteristic changes appear in the rising velocity Vr, the top portion velocity Vp, and the falling velocity Vf in the increasing/decreasing pattern of the carbon dioxide concentration value as the airway stenosis progresses, and conceived that the determination of the chronic obstructive pulmonary disease can be assisted by displaying information corresponding to these profile factors.

In FIG. 5A, the waveform information W that changes with the progress of the bronchial obstruction is displayed on the display section 15 (the dashed lines are illustrated as a reference and not actually displayed on the display section 15). It can be seen that as the bronchial obstruction progresses, the rising velocity Vr decreases and the top portion velocity Vp increases while the falling velocity Vf substantially unchanges.

Values of the rising velocity Vr, the top portion velocity Vp, and the falling velocity Vf may be displayed on the display section 15. In this case, the value of the most recently obtained profile factor (the value obtained for the rightmost increasing-decreasing pattern) is displayed. Thus, by referring to these values, medical workers may be assisted in determining chronic obstructive pulmonary disease.

Additionally or alternatively, an indicator indicating the chronological change of each value may be displayed on the display 15. In this example, an arrow indicating the increase or decrease of the value of the most recently obtained profile factor (the value obtained for the rightmost increasing-decreasing pattern) with respect to the value of the previously obtained profile factor (the value obtained for the center increasing-decreasing pattern) is displayed as an example of the indicator. In addition to or instead of the arrow, the color of at least one of the text indicating the type of the profile factor and the text indicating the value of the profile factor may be changed in accordance with the increase or decrease.

In the this example, when the increase or decrease of the value of the most recently obtained profile factor with respect to the value of the previously obtained profile factor is less than a predetermined value, it is indicated by a horizontal arrow. In addition to or instead of such an arrow, at least one of the text indicating the type of the profile factor and the text indicating the value of the profile factor may be displayed in a color different from that in the case where the increase or decrease of the value is no less than the predetermined value. The indicator illustrated in the other drawings may be displayed in the same or similar manner with the indicator as exemplified above.

According to such a configuration, the trend of each of the chronological changes of the rising velocity Vr, the top portion velocity Vp, and the falling velocity Vf can be visually recognized more intuitively. Therefore, it is possible to enhance the assistability for the determination of the chronic obstructive pulmonary disease.

As shown in FIG. 5B, each time the value of the profile factor is obtained, that is, the value of the profile factor may be displayed in association with each of a plurality of increasing-decreasing patterns displayed on the display section 15. According to such a configuration, it is possible to easily grasp a longer-term trend of each of the chronological changes of the rising velocity Vr, the top portion velocity Vp, and the falling velocity Vf. Therefore, it is possible to enhance the assistability for the determination of the chronic obstructive pulmonary disease.

Additionally or alternatively, as shown in FIG. 5C, each of the chronological changes of the rising velocity Vr, the top portion velocity Vp, and the falling velocity Vf in the time slot displayed on the display section 15 may be displayed in a graph format. Even with such a configuration, it is possible to easily grasp a longer-term trend of each of the chronological changes of the rising velocity Vr, the top portion velocity Vp, and the falling velocity Vf. Therefore, it is possible to enhance the assistability for the determination of the chronic obstructive pulmonary disease.

Figure 6A:
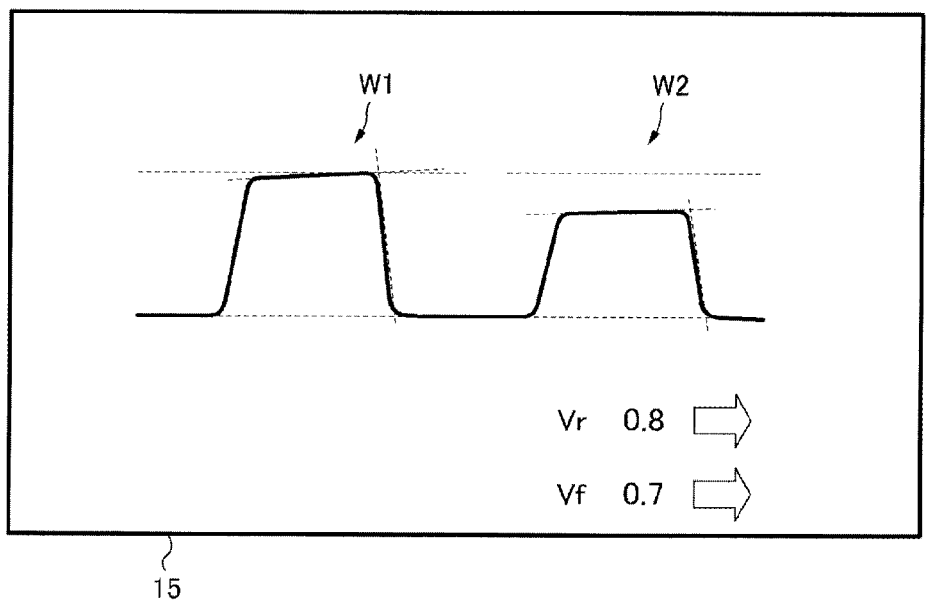
FIG. 6A illustrates a fourth operation example of a display section in the vital information displaying device.
Figure 6B:
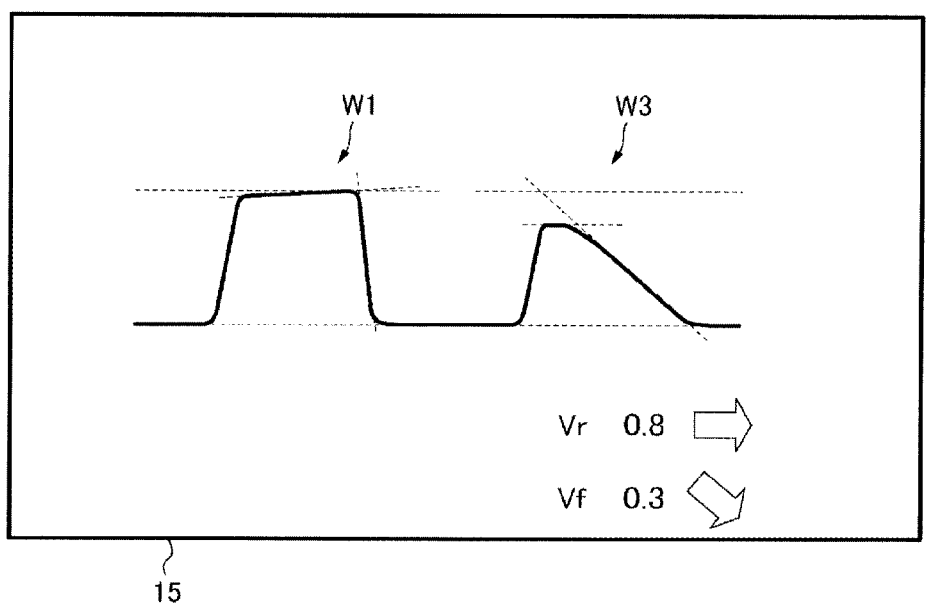
FIG. 6B illustrates the fourth operation example of the display section in the vital information displaying device.

FIGS. 6A and 6B illustrate a fourth example in which the rising velocity Vr and the falling velocity Vf are obtained as the profile factors. In this example, these profile factors are used to set a proper ventilation volume in the respirator.

When a respirator is used for neonates, exhaled respiration gas may leak to the outside without returning to the respirator because an intubation tube without a cuff is typically used. On the other hand, if the setting is made to increase the ventilation volume in view of the existence of the leakage, hyperventilation may occur in the subject. With the conventional device that obtains a maximum value of the carbon dioxide concentration and a respiration rate per unit time, it is difficult to distinguish the cause of the decrease in the value of the carbon dioxide concentration is due to the leakage in the respiration circuit or the hyperventilation occurring in the subject. The inventor of the present application noticed that the rising velocity Vr and the falling velocity Vf in the increasing-decreasing pattern of the carbon dioxide concentration value differ between the case where the leakage occurs in the respiratory circuit and the case where the hyperventilation occurs in the subject, and conceived that the distinction between the two cases can be assisted by displaying information corresponding to these profile factors.

In FIG. 6A, the waveform information W1 indicates a increasing-decreasing pattern of the carbon dioxide concentration value in the respiration gas of the subject connected to the normal respiratory circuit. The waveform information W2 indicates a increasing-decreasing pattern of the carbon dioxide concentration value in the respiration gas of the subject who has hyperventilated. In this case, it can be seen that the peak value of the carbon dioxide concentration decreases while the rising velocity Vr and the falling velocity Vf substantially unchange. In FIG. 6B, the waveform information W3 indicates an increasing-decreasing pattern of the carbon dioxide concentration value in the respiration gas of the subject connected to the respiratory circuit in which leakage has occurred. Comparing with the normal waveform information W1, it is understood that the peak value of the carbon dioxide concentration and the falling velocity Vf decreases while the rising velocity Vr substantially unchanges.

Values of the rising velocity Vr and the falling velocity Vf may be displayed on the display section 15. In this case, the value of the most recently obtained profile factor is displayed. Thus, by referring to these values, medical workers can distinguish the cause of the decrease in the peak value of the carbon dioxide concentration, and can be assisted in setting the proper ventilation volume in the respirator.

Additionally or alternatively, an indicator indicating the chronological change of each value may be displayed on the display 15. In this example, an arrow indicating an increase or decrease in the value of the most recently obtained profile factor with respect to the value of the previously obtained profile factor is displayed as an example of the indicator. In addition to or instead of the arrow, the color of at least one of the text indicating the type of the profile factor and the text indicating the value of the profile factor may be changed in accordance with the increase or decrease.

According to such a configuration, the trend of each of the chronological changes of the rising velocity Vr and the falling velocity Vf can be visually recognized more intuitively. Therefore, it is possible to enhance the assistability for setting a proper ventilation volume in the respirator.

As in the examples shown in FIG. 3B, FIG. 4B, and FIG. 5B, each time the value of the profile factor is obtained, that is, the value of the profile factor may be displayed in association with each of a plurality of increasing-decreasing patterns displayed on the display section 15. According to such a configuration, it is possible to easily grasp a longer-term trend of each of the chronological changes of the rising velocity Vr and the falling velocity Vf. Therefore, it is possible to enhance the assistability for setting a proper ventilation volume in the respirator.

Additionally or alternatively, as shown in FIG. 3C, FIG. 4C, and FIG. 5C, each of the chronological changes of the rising velocity Vr and the falling velocity Vf in the time slot displayed on the display section 15 may be displayed in a graph format. Even with such a configuration, it is possible to easily grasp a longer-term trend of each of the chronological changes of the rising velocity Vr and the falling velocity Vf. Therefore, it is possible to enhance the assistability for setting a proper ventilation volume in the respirator.

Figure 7A:
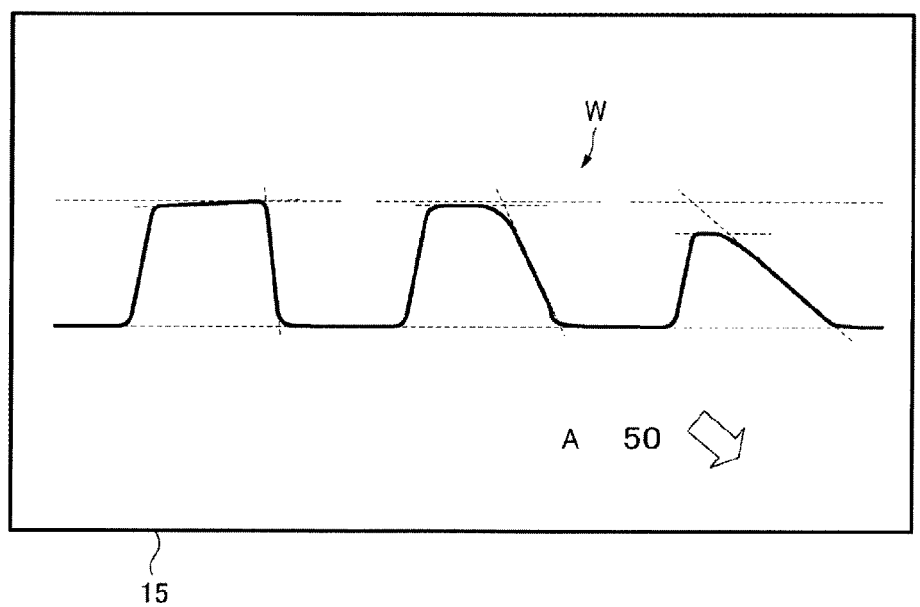
FIG. 7A illustrates a fifth operation example of a display section in the vital information displaying device.

FIG. 7A shows a fifth example in which the under-waveform area A is obtained as the profile factor. In this example, the profile factor is used to determine a change in the ventilation state of the subject or a respiratory circuit abnormality in the respirator.

When a respirator is used for neonates, exhaled respiration gas may leak to the outside without returning to the respirator because an intubation tube without a cuff is typically used. With the conventional device that obtains a maximum value of the carbon dioxide concentration and a respiration rate per unit time, it is difficult to judge whether the cause of the decrease in the value of the carbon dioxide concentration is due to an increase in the leakage in the respiration circuit or a decrease in the ventilation rate of the subject. The leak rate increases with both increased leakage and decreased ventilation. The inventor of the present application noticed that a characteristic change appears in the under-waveform area A in the increasing-decreasing pattern in the carbon dioxide concentration value as the leak rate in the respiratory circuit increases, and conceived that by displaying information corresponding to this profile factor, it is possible to assist the determination of the change in the ventilation state of the subject and the respiratory circuit abnormality.

In FIG. 7A, the waveform information W that changes with the increase of the leak rate is displayed on the display section 15 (the dashed lines are illustrated as a reference and not actually displayed on the display section 15). It can be seen that the under-waveform area A decreases with an increase in the leak rate or a decrease in the ventilation volume of the subject.

The value of the under-waveform area A may be displayed on the display section 15. In this case, the value of the most recently obtained profile factor (the value obtained for the rightmost increasing-decreasing pattern) is displayed. Thus, by referring to this value, medical workers may be assisted in determining the change in the ventilation state of the subject and the respiratory circuit abnormality in the respirator.

Additionally or alternatively, an indicator indicating the chronological change of the value of the under-waveform area A may be displayed on the display section 15. In this example, an arrow indicating the increase or decrease of the value of the most recently obtained profile factor (the value obtained for the rightmost increasing-decreasing pattern) with respect to the value of the previously obtained profile factor (the value obtained for the center increasing-decreasing pattern) is displayed as an example of the indicator. In addition to or instead of the arrow, the color of at least one of the text indicating the type of the profile factor and the text indicating the value of the profile factor may be changed in accordance with the increase or decrease.

According to such a configuration, the trend of the chronological change of the under-waveform area A can be visually recognized more intuitively. Therefore, it is possible to enhance the assistability for the determination of the change in the ventilation state of the subject and the respiratory circuit abnormality in the respirator.

Figure 7B:
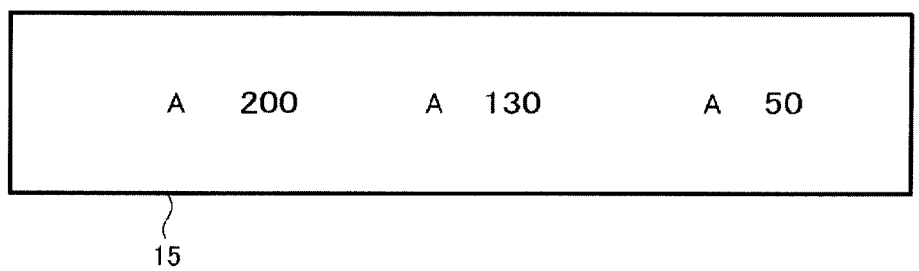
FIG. 7B illustrates the fifth operation example of the display section in the vital information displaying device.

As shown in FIG. 7B, each time the value of the profile factor is obtained, that is, the value of the profile factor may be displayed in association with each of a plurality of increasing-decreasing patterns displayed on the display section 15. According to such a configuration, it is possible to easily grasp a longer-term trend of the chronological change of the under-waveform area A. Therefore, it is possible to enhance the assistability for the determination of the change in the ventilation state of the subject and the respiratory circuit abnormality in the respirator.

Figure 7C:
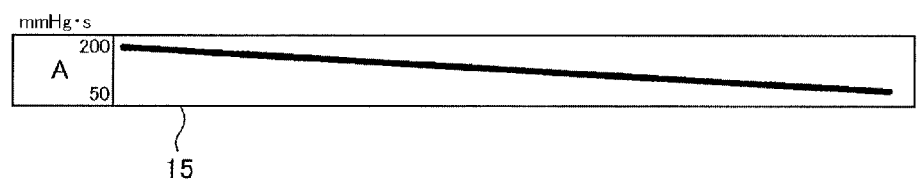
FIG. 7C illustrates the fifth operation example of the display section in the vital information displaying device.

Additionally or alternatively, as shown in FIG. 7C, the chronological change of the under-waveform area A in the time slot displayed on the display section 15 may be displayed in the form of a graph. Even with such a configuration, a longer-term trend of the chronological change of the under-waveform area A can be easily grasped. Therefore, it is possible to improve the assistability for determining a respiratory circuit abnormality in the respirator.

Figure 8A:
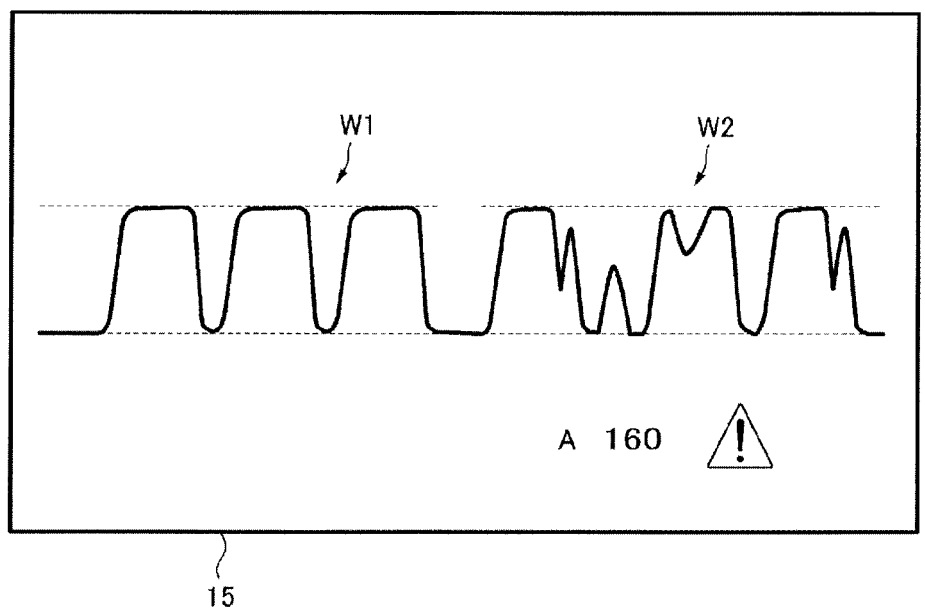
FIG. 8A illustrates a sixth operation example of a display section in the vital information displaying device.

FIG. 8A shows a sixth example in which the under-waveform area A is obtained as the profile factor. In this example, this profile factor is used to determine the ventilation state of a subject connected to a respirator.

Even in situations where the subject's respiration is controlled by the respirator, the subject's own spontaneous respiration may be mixed. The fact that the frequency of spontaneous respiration increases can be a diagnostic criterion for the fact that the respiratory function of the subject has been restored and the timing of withdrawal from the respirator is approaching. With the conventional device that obtains a maximum value of the carbon dioxide concentration and a respiration rate per unit time, it is difficult to clearly recognize the mixing of the spontaneous respiration from displayed values thus obtained. The inventor of the present application noticed that a characteristic change appears in the under-waveform area A in the increasing-decreasing pattern of the carbon dioxide concentration value when the spontaneous respiration of the subject is mixed, and conceived that the determination of the improvement of the ventilation state of the subject can be assisted by displaying information corresponding to this profile factor.

In FIG. 8A, the waveform information W1 indicates a increasing-decreasing pattern of the carbon dioxide concentration value in the respiration gas of the subject only by forced ventilation of the respirator. The waveform information W2 indicates a increasing-decreasing pattern of the carbon dioxide concentration value when the spontaneous respiration of the subject is added to the forced ventilation. It can be seen that the under-waveform area A is not constant with the mixing of spontaneous respiration.

The value of the under-waveform area A may be displayed on the display section 15. In this case, the value of the most recently obtained profile factor is displayed. Thus, by referring to this value, medical workers may be assisted in determining the subject's spontaneous respiration or improved ventilation.

Additionally or alternatively, an indicator indicating the chronological change of the value of the under-waveform area A may be displayed on the display section 15. In this example, an indicator indicating that the value of the under-waveform area A is not substantially constant is displayed. In addition to or instead of the indicator, the color of at least one of the text indicating the type of the profile factor and the text indicating the value of the profile factor may be changed to indicate that the value of the under-waveform area A is not substantially constant.

According to such a configuration, the trend of the chronological change of the under-waveform area A can be visually recognized more intuitively. Therefore, it is possible to improve the assistability for the determination of the improvement of the ventilation state.

As illustrated in FIG. 7B, each time the value of the profile factor is obtained, that is, the value of the profile factor may be displayed in association with each of a plurality of increasing-decreasing patterns displayed on the display section 15. According to such a configuration, it is possible to easily grasp a longer-term trend of the chronological change of the under-waveform area A. Therefore, it is possible to improve the assistability for the determination of the improvement of the ventilation state.

Figure 8B:
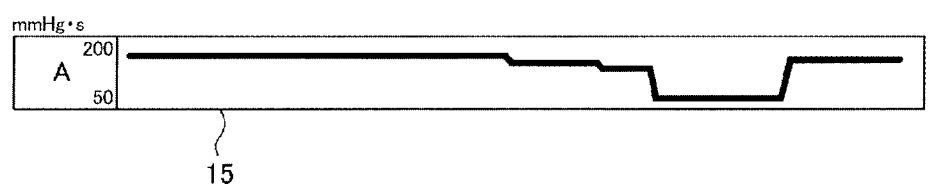
FIG. 8B illustrates the sixth operation example of the display section in the vital information displaying device.

Additionally or alternatively, as shown in FIG. 8B, the chronological change of the under-waveform area A in the time slot displayed on the display section 15 may be displayed in a graph form. Even with such a configuration, a longer-term trend of the chronological change of the under-waveform area A can be easily grasped. Therefore, it is possible to improve the assistability for the determination of the improvement of the ventilation state.

Figure 9A:
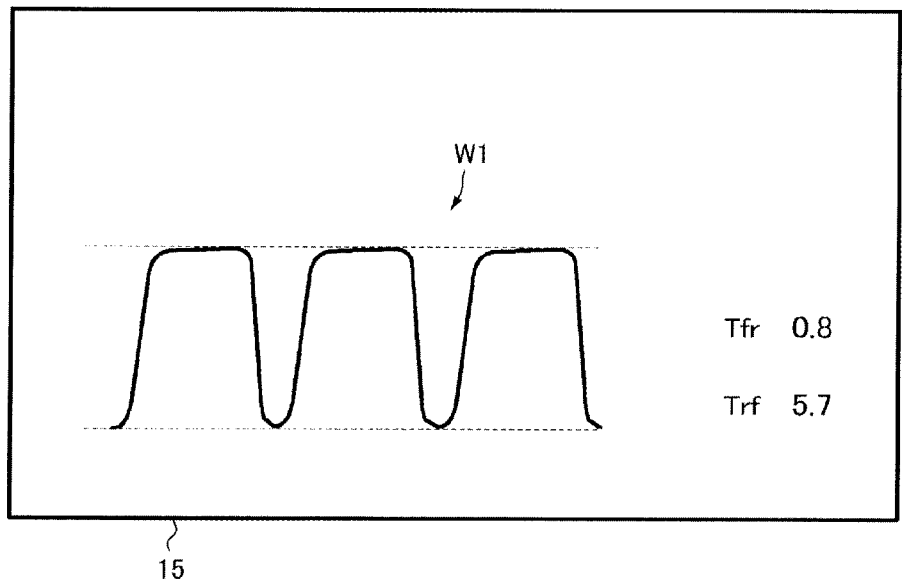
FIG. 9A illustrates a seventh operation example of a display section in the vital information displaying device.
Figure 9B:
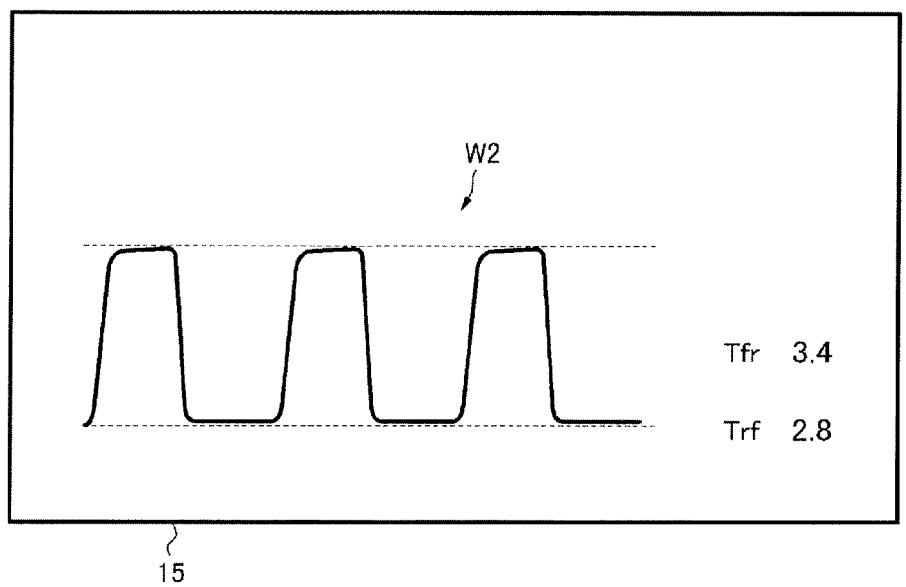
FIG. 9B illustrates the seventh operation example of the display section in the vital information displaying device.

FIGS. 9A and 9B illustrate a seventh example in which the rising-falling time interval Trf and the falling-rising time interval Tfr are obtained as the profile factors. In this example, these profile factors are used to determine the ventilation state of the subject.

In use of the respirator, respiration of the subject is controlled based on a preset I:E ratio. The I:E ratio represents the ratio of the inspiratory duration (I) to the expiratory duration (E). With the conventional device that obtains a maximum value of the carbon dioxide concentration and a respiration rate per unit time, it is difficult to clearly recognize the mixing of the spontaneous respiration from displayed values thus obtained. The inventor of the present application noticed that the difference between the rising-falling time interval Trf and the falling-rising time interval Tfr in the increasing-decreasing pattern of the carbon dioxide concentration value of the subject can be an index for determining the difference between the preset I:E ratio, and conceived that the determination of the ventilation state of the subject can be assisted by displaying information corresponding to these profile factors.

In FIG. 9A, the waveform information W1 indicates a increasing-decreasing pattern of the carbon dioxide concentration value in the respiration gas of the subject connected to the respirator in which the I:E ratio is preset to 1:2. In FIG. 9B, the waveform information W2 indicates a increasing-decreasing pattern of the carbon dioxide concentration value in the respiration gas of the subject connected to the respirator in which the I:E ratio is preset to 1:1.

Values of the rising-falling time interval Trf and the falling-rising time interval Tfr may be displayed on the display section 15. In this case, the value of the most recently obtained profile factor is displayed. The rising-falling time interval Trf may be associated with an expiratory duration (E). The falling-rising time interval Tfr may be associated with an inspiratory duration (I). Therefore, medical workers can recognize the actual I:E ratio of the subject by referring to these values. By comparing the actual I:E ratio with the I:E ratio preset in the respirator, the determination of the ventilation state of the subject may be assisted.

It should be noted that a ratio of the rising-falling time interval Trf and the falling-rising time interval Tfr may be displayed on the display section 15.

Figure 10A:
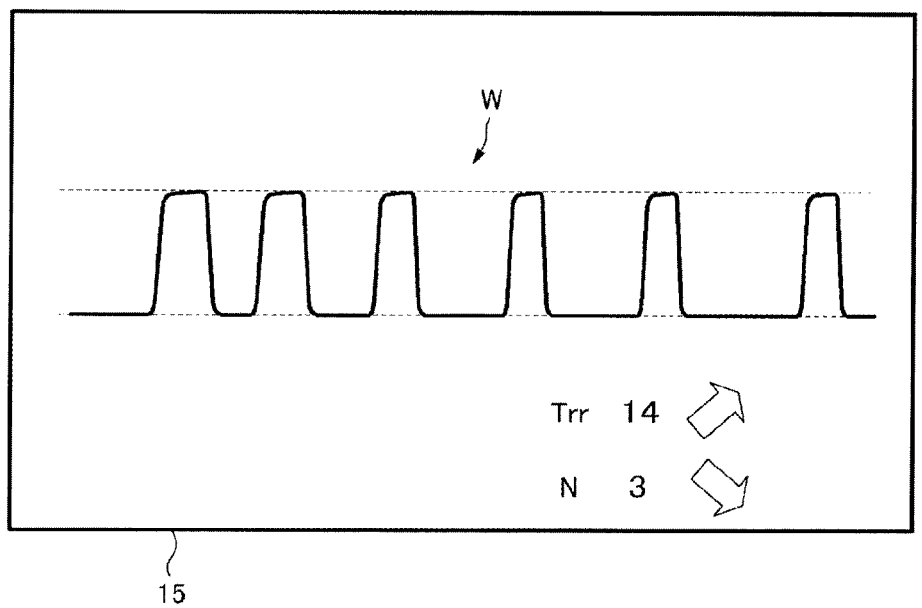
FIG. 10A illustrates an eighth operation example of a display section in the vital information displaying device.

FIG. 10A shows an eighth example in which the rising-rising time interval Trr is obtained as a profile factor. In this example, the profile factor is used to determine respiratory depression that has occurred in the subject.

Respiratory depression may occur in the subject after surgery or sedation. The respiratory depression decreases the respiratory rate. With the conventional device that obtains a maximum value of the carbon dioxide concentration and a respiration rate per unit time, it is difficult to clearly determine whether the cause of the decrease in respiration rate is due to respiratory depression. The inventor of the present application noticed that a characteristic change appears in the rising-rising time interval Trr in the increasing-decreasing pattern of the carbon dioxide concentration value when respiratory depression occurs in the subject, and conceived that the determination of respiratory depression can be assisted by displaying information corresponding to this profile factor.

FIG. 10A shows waveform information W obtained when respiratory depression occurs in the subject. It can be seen that the rising-rising time interval Trr is gradually prolonged before a remarkable decreasing trend is observed in the respiration rate N.

Values of the rising-rising time interval Trr and the respiration rate N may be displayed on the display section 15. In this case, the value of the most recently obtained profile factor is displayed. Thus, medical workers may be assisted in determining respiratory depression that has occurred in the subject by referring to these values.

Additionally or alternatively, an indicator indicating the chronological change of each value may be displayed on the display 15. In this example, an arrow indicating an increase or decrease in the value of the most recently obtained profile factor with respect to the value of the previously obtained profile factor is displayed as an example of the indicator. In addition to or instead of the arrow, the color of at least one of the text indicating the type of the profile factor and the text indicating the value of the profile factor may be changed in accordance with the increase or decrease.

According to such a configuration, the trend of each of the chronological changes of the rising-rising time interval Trr and the respiration rate N can be visually recognized more intuitively. Therefore, it is possible to improve the assistability for the determination of the respiratory depression that has occurred in the subject.

Further, in this example, the appearance of the indicator is changed in accordance with the extent of the chronological change. More specifically, since the chronological change of the respiration rate N has a greater extent than the chronological change of the rising-rising time interval Trr, the color of the arrow is changed. According to such a configuration, the trend of each of the chronological changes of the rising-rising time interval Trr and the respiration rate N can be grasped in more detail. The indicator illustrated in the other drawings may be displayed in the same or similar manner with the indicator as exemplified above. The extent of the chronological change may be represented by changing the angle of the arrow. Alternatively, the type of the indicator to be displayed may be changed in accordance with the extent of the chronological change.

As in the examples shown in FIG. 3B, FIG. 4B, FIG. 5B, and FIG. 7B, each time the value of the profile factor is obtained, that is, the value of the profile factor may be displayed in association with each of a plurality of increasing-decreasing patterns displayed on the display section 15. According to such a configuration, it is possible to easily grasp a longer-term trend of each of the chronological changes of the rising-rising time interval Trr and the respiration rate N. Therefore, it is possible to improve the assistability for the determination of the respiratory depression that has occurred in the subject.

Figure 10B:
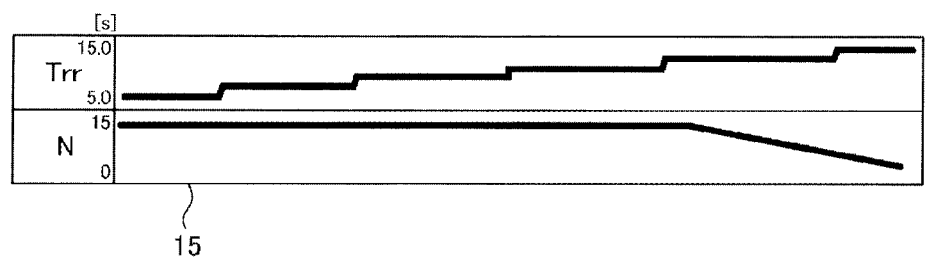
FIG. 10B illustrates the eighth operation example of the display section in the vital information displaying device.

Additionally or alternatively, as shown in FIG. 10B, each of the chronological changes of the rising-rising time interval Trr and the respiration rate N in the time slot displayed on the display section 15 may be displayed in a graph format. Even with such a configuration, a longer-term trend of each of the chronological changes of the rising-rising time interval Trr and the respiration rate N can be easily grasped. Therefore, it is possible to improve the assistability for the determination of the respiratory depression that has occurred in the subject.

Instead of the rising-rising time interval Trr, a falling-falling time interval Tff may be displayed on the display section 15. The same determination can be made based on the falling-falling time interval Tff.

As shown in FIG. 1, the vital information displaying device 1 may include a notifier 16. The notifier 16 is configured to perform notification when the value of the obtained profile factor is not within a predetermined threshold range. The notification is performed through at least one of a visual notification, an auditory notification, and a tactile notification. The threshold range may be appropriately determined in accordance with an item to be determined. The mode of notification may be configured to differ depending on the type of profile factor for which the value is not within the threshold range.

For example, in the fourth example shown in FIG. 6 and the fifth example shown in FIG. 7, when the falling velocity Vf and the under-waveform area A fall below a predetermined value, the notification by the notifier 16 may be performed. The predetermined value may be defined as a value corresponding to a case where the extent of the leak rate needs to be confirmed or is in an unacceptable state. According to such a configuration, it is possible to prevent the subject from falling into a low ventilation state due to an increase in the leak rate.

The threshold range may be determined based on a combination of a plurality of profile factors. For example, in the first example shown in FIG. 3, when the rising angle [theta]r is lower than a predetermined value and the top portion angle [theta]p is higher than a predetermined value, the notification by the notifier 16 may be performed. The predetermined value may be defined as a value corresponding to a case where the progress of the airway stenosis needs to be confirmed or is not acceptable. According to such a configuration, the progress of the airway stenosis occurring in the subject can be confirmed at an early stage.

That is, according to the configuration as described above, by obtaining at least one profile factor, it is possible to prevent the occurrence of an abnormality in the item to be determined or to recognize the occurrence of the abnormality at an early stage.

The above embodiment is merely exemplary to facilitate understanding of the presently disclosed subject matter. The configuration according to the above embodiment can be appropriately modified or improved without departing from the fundamental concept of the presently disclosed subject matter.

In the above embodiment, all of the obtained values of the profile factors are subjected to the display on the display section 15. However, the obtained value of the profile factor may be displayed on the display section only when the obtained value is not within the predetermined threshold range or when the value indicates a trend that deviates from the threshold range.

The type of the profile factor to be displayed may be selected by a user via a user interface (not illustrated). The instruction relating to the selection is input to the input interface 11, and is processed by the processor 12.

The type of the profile factor to be displayed may be determined in advance in accordance with the attribute information of the subject, such as medical history, age, sex, clinical department, smoking, and the like. In other words, correspondence between the attribute information of the subject and the type of the profile factor to be displayed on the display section 15 may be determined in advance.

For example, when attribute information indicating that the subject has a history of chronic obstructive pulmonary disease is input to the input interface 11, the processor 12 may automatically perform setting so that information relating to a specific profile factor (e.g., at least one of a value of at least one of a value, a chronological change thereof and an indicator indicating the chronological change of at least one of the rising angle [theta]r and the top portion angle [theta]p) is displayed whereas information relating to other profile factors is not displayed. The information related to the profile factor that is displayed based on the predetermined correspondence may be changed according to the user's request via the user interface described above.

The type of the profile factor to be displayed may be determined in advance in accordance with the vital information different from the vital information related to the obtained waveform information W. In this case, a plurality of sensors S or a plural kinds of sensors S may be connected to the input interface 11.

For example, based on a signal input to the input interface 11 from another sensor S, it is possible to determine an abnormality in value or a trend deviating from a normal value range of vital information related to an electrocardiogram or blood pressure. In this case, the processor 12 may automatically perform the setting so that the information relating to the specific profile factor (e.g., at least one of a value of at least one of a value, a chronological change thereof and an indicator indicating the chronological change of the under-waveform area A) is displayed whereas information relating to other profile factors is not displayed. By considering the under-waveform area A of the waveform information W in association with the abnormality of the vital information related to the electrocardiogram or the blood pressure, it is possible to determine, for example, a decrease in the ventilation rate due to a decrease in the pulmonary blood flow rate of the subject. The information related to the profile factor that is displayed based on the predetermined correspondence may be changed according to the user's request via the user interface described above.

The type of the profile factor to be displayed may be determined in advance in accordance with the operation parameter information of an external medical device that is different from the vital information displaying device 1. As the external medical device, the respirator may be exemplified. As the operation parameter information, the ventilation rate and the leak rate may be exemplified. In this case, the vital information displaying device 1 and the respirator are connected so as to be able to communicate with each other, so that a signal corresponding to the operation parameter information is input to the input interface 11.

For example, when a signal corresponding to the ventilation rate or the leak rate is input to the input interface 11, the processor 12 may automatically perform setting so that information relating to a specific profile factor (e.g., at least one of a value of at least one of a value, a chronological change thereof and an indicator indicating the chronological change of at least one of the rising angle [theta]r and the top portion angle [theta]p) is displayed whereas information relating to other profile factors is not displayed. The operation parameter information may also be displayed on the display section 15. By considering the profile factor of the subject's carbon dioxide concentration value in association with the operation parameter information of the respirator, it is possible to assist the determination of the cause of the decrease in the carbon dioxide concentration value. The information related to the profile factor that is displayed based on the predetermined correspondence may be changed according to the user's request via the user interface described above.

In the above embodiment, the processor 12 for obtaining the value of the profile factor of the waveform information W and the display section 15 for displaying the normalized waveform information WN are provided in the same device. However, the acquisition of the value of the profile factor and the display of the information corresponding to the value may be performed by independent devices.

Figure 11:
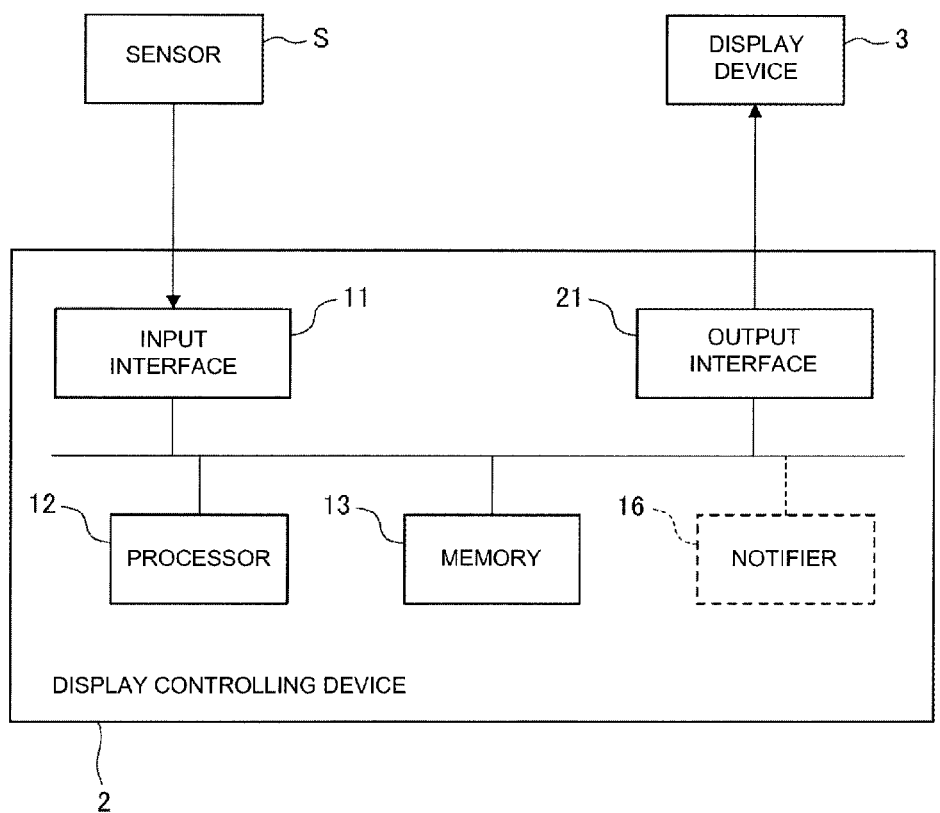
FIG. 11 illustrates a configuration of a display controlling device according to an embodiment.

FIG. 11 illustrates a display controlling device 2 capable of realizing such an operation. Components substantially the same as those of the vital information displaying device 1 illustrated in FIG. 1 are denoted by the same reference numerals. Repetitive descriptions for those will be omitted.

The display controlling device 2 may be connected to a display device 3 via a communication network. The display controlling device 2 includes an output interface 21. The processor 12 may cause the output interface 21 to output a control signal for causing the display device 3 to display information corresponding to the obtained profile factor value.

In the above embodiment, the carbon dioxide concentration (partial pressure) in the respiration gas is exemplified as vital information of the subject. However, the above configuration can be applied to the display of the vital information that exhibits temporal variation while the same trend of variations repeatedly appears. As such vital information, concentration (partial pressure) of oxygen or anesthetic gas in the respiration gas, a flow of the respiration gas, a volume of the respiration gas, pulse wave, electrocardiogram (ECG), and electroencephalogram (EEG).

The present application is based on Japanese Patent Application No. 2018-036671 filed on Mar. 1, 2018 and Japanese Patent Application No. 2018-244985 filed on Dec. 27, 2018, the entire contents of which are hereby incorporated by reference.

The invention claimed is:

1. A vital information displaying device comprising:
an input interface configured to receive a signal corresponding to vital information of a subject that is detected through a sensor and exhibits temporal variation;
a processor;
a memory configured to store at least one instruction that is executable by the processor; and
a display section,
wherein when the at least one instruction is executed by the processor, waveform information is generated based on the signal;
wherein a value of a profile factor of the waveform information is obtained every time a predetermined time period is elapsed;
wherein at least one of the value of the profile factor as obtained, a chronological change of the value, and an indicator indicating the chronological change is displayed on the display section, as profile factor information;

wherein the profile factor includes at least one of a rising angle, a top portion angle, a falling angle, a rising velocity, an absolute value of the rising velocity, a top portion velocity, an absolute value of the top portion velocity, a falling velocity, an absolute angle of the falling velocity, an under-waveform area, a rising-falling time interval, a falling-rising time interval, a rising-rising time interval and a falling-falling time interval;

wherein a correspondence between a type of the profile factor to be displayed on the display section and additional information is determined in advance;

wherein the additional information includes at least one attribute information of the subject and other vital information that is different from the vital information based on a signal input from another sensor;

wherein the input interface is configured to receive, via a user interface, a user's request for changing the profile factor information that is to be displayed on the display section; and wherein the processor is configured to, in response to reception of the additional information by the input interface, cause the display section to display the profile factor information of a specific profile factor based on the correspondence, while causing the display section not to display the profile factor information of other profile factor.

2. The vital information displaying device according to claim 1, wherein when the at least one instruction is executed by the processor, the indicator is changed in accordance with an extent of the chronological change of the value.

3. The vital information displaying device according to claim 1, further comprising:
a notifier configured to perform a notification in a case where the value is not within a predetermined threshold range.

4. The vital information displaying device according to claim 1, wherein the vital information is a partial pressure or a concentration of carbon dioxide or oxygen contained in respiration gas.

5. A display controlling device comprising:
an input interface configured to receive a signal corresponding to vital information of a subject that is detected through a sensor and exhibits temporal variation;
a processor;
a memory configured to store at least one instruction that is executable by the processor; and
an output interface,
wherein when the at least one instruction is executed by the processor, waveform information is generated based on the signal;
wherein a value of a profile factor of the waveform information is obtained every time a predetermined time period is elapsed;
wherein a control signal is output from the output interface to cause a display device to display at least one of the value of the profile factor as obtained, a chronological change of the value, and an indicator indicating the chronological change, as profile factor information;
wherein the profile factor includes at least one of a rising angle, a top portion angle, a falling angle, a rising velocity, an absolute value of the rising velocity, a top portion velocity, an absolute value of the top portion velocity, a falling velocity, an absolute angle of the falling velocity, an under-waveform area, a rising-falling time interval, a falling-rising time interval, a rising-rising time interval and a falling-falling time interval;
wherein a correspondence between a type of the profile factor to be displayed on a display section and additional information is determined in advance;
wherein the additional information includes at least one of attribute information of the subject and other vital information that is different from the vital information based on a signal input from another sensor;
wherein the input interface is configured to receive, via a user interface, a user's request for changing the profile factor information that is to be displayed on the display section; and
wherein the control signal is output, in response to reception of the additional information by the input interface, to cause the display section to display the profile factor information of a specific profile factor based on the correspondence, while causing the display section not to display the profile factor information of other profile factor.

6. A non-transitory computer-readable medium having stored a computer program including at least one instruction to be executed by a processor of a display controlling device provided with an input interface configured to receive a signal corresponding to vital information of a subject that is detected through a sensor and exhibits temporal variation,
wherein when the at least one instruction is executed by the processor, waveform information is generated based on the signal;
wherein a value of a profile factor of the waveform information is obtained every time a predetermined time period is elapsed;
wherein a control signal is output from the output interface to cause a display device to display at least one of the value of the profile factor as obtained, a chronological change of the value, and an indicator indicating the chronological change, as profile factor information;
wherein the profile factor includes at least one of a rising angle, a top portion angle, a falling angle, a rising velocity, an absolute value of the rising velocity, a top portion velocity, an absolute value of the top portion velocity, a falling velocity, an absolute angle of the falling velocity, an under-waveform area, a rising-falling time interval, a falling-rising time interval, a rising-rising time interval and a falling-falling time interval;
wherein a correspondence between a type of the profile factor to be displayed on the display section and additional information is determined in advance;
wherein the input interface is configured to receive, via a user interface, a user's request for changing the profile factor information that is to be displayed on the display section; and
wherein the control signal is output, in response to reception of the additional information by the input interface, to cause the display section to display the profile factor information of a specific profile factor based on the correspondence, while causing the display section not to display the profile factor information of other profile factor.

* * * * *